(12) United States Patent
Kaiser et al.

(10) Patent No.: US 7,255,700 B2
(45) Date of Patent: Aug. 14, 2007

(54) DEVICE AND METHOD OF FASTENING A GRAFT TO A BONE

(75) Inventors: Ryan A Kaiser, Leesburg, IN (US); Jason D Meridew, Syracuse, IN (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 226 days.

(21) Appl. No.: 10/464,037

(22) Filed: Jun. 18, 2003

(65) Prior Publication Data

US 2004/0260296 A1    Dec. 23, 2004

(51) Int. Cl.
*A61B 17/58* (2006.01)

(52) U.S. Cl. .................................... 606/72

(58) Field of Classification Search ............ 606/72–73, 606/76–77, 61–66, 151, 232; 411/344, 352–53, 411/516, 17, 19, 935, 947
See application file for complete search history.

(56) References Cited

U.S. PATENT DOCUMENTS

| | | | |
|---|---|---|---|
| 1,039,576 A | | 9/1912 | Mueller |
| 1,547,162 A | | 7/1925 | Bohlman |
| 1,677,269 A | | 7/1928 | Burghart |
| 3,664,345 A | | 5/1972 | Dabbs et al. |
| 4,262,665 A | * | 4/1981 | Roalstad et al. ............ 606/62 |
| 4,537,185 A | * | 8/1985 | Stednitz ..................... 606/73 |
| 4,834,752 A | | 5/1989 | Van Kampen |
| 4,988,351 A | * | 1/1991 | Paulos et al. .............. 606/72 |
| 5,013,313 A | * | 5/1991 | Surer ........................ 606/60 |
| 5,092,887 A | | 3/1992 | Gendler |
| 5,129,902 A | | 7/1992 | Goble et al. |
| 5,151,104 A | * | 9/1992 | Kenna ...................... 606/73 |
| 5,152,790 A | * | 10/1992 | Rosenberg et al. ...... 623/13.14 |
| 5,258,015 A | | 11/1993 | Li et al. |
| 5,306,290 A | | 4/1994 | Martins et al. |
| 5,306,301 A | | 4/1994 | Graf et al. |
| 5,352,229 A | | 10/1994 | Goble et al. |
| 5,409,490 A | | 4/1995 | Ethridge |
| 5,456,722 A | | 10/1995 | McLeod et al. |
| 5,487,685 A | | 1/1996 | Stillbäck et al. |
| 5,628,756 A | | 5/1997 | Barker, Jr. et al. |
| 5,630,824 A | | 5/1997 | Hart |
| 5,632,748 A | | 5/1997 | Beck, Jr. et al. |
| 5,664,922 A | | 9/1997 | Janssen et al. |
| 5,697,929 A | | 12/1997 | Mellinger |
| 5,702,398 A | | 12/1997 | Tarabishy |
| 5,718,706 A | | 2/1998 | Roger |
| 5,749,669 A | * | 5/1998 | Ketteler ................... 403/12 |
| 5,782,866 A | | 7/1998 | Wenstrom, Jr. |

(Continued)

*Primary Examiner*—Eduardo C. Robert
*Assistant Examiner*—Annette Reimers
(74) *Attorney, Agent, or Firm*—Harness, Dickey, Pierce, P.L.C.

(57) ABSTRACT

A device and method for fastening one or more graft strands to a bone. The device may include a first member having a first opening and a second member having a second opening. The first member may include a plurality of radial projections defining recesses, wherein each graft is separately received in a corresponding recess. The device may also include a fastener passing through the first and second openings. The fastener may have a first portion engaging the first member and a second portion received into the bone, such that tightening the fastener against the first member compresses the graft strands between opposing faces of the first and second members.

35 Claims, 5 Drawing Sheets

U.S. PATENT DOCUMENTS

| | | | |
|---|---|---|---|
| 5,928,236 A | 7/1999 | Augagneur et al. | |
| 5,931,869 A | 8/1999 | Boucher et al. | |
| 5,964,767 A * | 10/1999 | Tapia et al. | 606/73 |
| 6,004,349 A | 12/1999 | Jackson | |
| 6,036,704 A * | 3/2000 | Yoon | 606/153 |
| 6,056,752 A | 5/2000 | Roger | |
| 6,086,608 A | 7/2000 | Ek et al. | |
| 6,093,201 A | 7/2000 | Cooper et al. | |
| 6,126,677 A | 10/2000 | Ganaja et al. | |
| 6,132,442 A | 10/2000 | Ferragamo et al. | |
| 6,162,234 A * | 12/2000 | Freedland et al. | 606/151 |
| 6,179,841 B1 | 1/2001 | Jackson | |
| 6,214,007 B1 | 4/2001 | Anderson | |
| 6,235,058 B1 * | 5/2001 | Huene | 623/13.14 |
| 6,273,890 B1 | 8/2001 | Frazier et al. | |
| 6,280,472 B1 | 8/2001 | Boucher et al. | |
| 6,325,804 B1 | 12/2001 | Wenstrom | |
| 6,336,940 B1 | 1/2002 | Graf et al. | |
| 6,355,066 B1 | 3/2002 | Kim | |
| 6,364,880 B1 | 4/2002 | Michelson | |
| 6,368,326 B1 | 4/2002 | Dakin et al. | |
| 6,371,958 B1 * | 4/2002 | Overaker | 606/72 |
| 6,379,363 B1 * | 4/2002 | Herrington et al. | 606/79 |
| 6,383,187 B2 | 5/2002 | Törmälä et al. | |
| 6,419,700 B2 | 7/2002 | Huene | |
| 6,432,123 B2 | 8/2002 | Schwartz et al. | |
| 6,464,706 B1 | 10/2002 | Winters | |
| 6,482,232 B1 | 11/2002 | Boucher et al. | |
| 6,517,579 B1 | 2/2003 | Paulos et al. | |
| 6,533,802 B2 | 3/2003 | Bojarski et al. | |
| 6,558,389 B2 | 5/2003 | Clark et al. | |
| 6,562,043 B1 | 5/2003 | Chan | |
| 6,562,044 B1 | 5/2003 | Cooper | |
| 6,569,186 B1 | 5/2003 | Winters et al. | |
| 6,685,707 B2 * | 2/2004 | Roman et al. | 606/72 |
| 2001/0053913 A1 * | 12/2001 | Freedland | 606/73 |
| 2002/0042615 A1 | 4/2002 | Graf et al. | |
| 2003/0083662 A1 * | 5/2003 | Middleton | 606/72 |
| 2003/0125743 A1 * | 7/2003 | Roman et al. | 606/72 |

* cited by examiner

DEVICE AND METHOD OF FASTENING A GRAFT TO A BONE

BACKGROUND OF THE INVENTION

Ligaments are strong fibrous soft tissue connecting the articular ends of bones to bind them together and to facilitate or limit motion. Injuries to ligaments are common, and patients who are physically active are generally more susceptible to such ligament injuries. The anterior cruciate ligament (ACL) of the knee joint is a ligament frequently injured by such patients. ACL injuries cause instability in the knee joint which, when left untreated, may lead to degenerative arthritis. Because of this condition, ACL reconstruction may be required. Generally during ACL reconstruction, a substitute soft tissue ligament or graft is attached to the femur (femoral fixation) and/or to the tibia (tibial fixation) to facilitate regrowth and permanent attachment.

There are several known methods for performing ACL reconstruction, and there are also several tibial or femoral fixation devices that may be used with these methods, some of which are reviewed in U.S. Pat. No. 6,482,232. Nevertheless, new methods and devices that reduce soft tissue damage, are easy to install, prevent slippage of the graft, promote healing and increase strength are still needed.

SUMMARY

One embodiment of the invention provides a device for fastening one or more graft strands to a bone. The device may include a first member having a first opening and a second member having a second opening. The first member may include a plurality of radial projections defining recesses, and each graft may be separately received in a corresponding recess. The device may also include a fastener passing through the first and second openings. The fastener may have a first portion engaging the first member and a second portion received into the bone, such that tightening the fastener against the first member compresses the graft strands between opposing faces of the first and second members. Moreover, while the present invention is discussed in detail in relation to ACL reconstruction, it will be understood that the invention may be used to secure any type of soft tissue.

Another embodiment of the invention provides a device for fastening one or more graft strands to a bone and may includes an annular member that has a central opening, and a fastener that may have a head and a body. The annular member includes a plurality of radial projections defining recesses, such that each graft may be separately received in a corresponding recess. The body of the fastener may pass through the central opening of the annular member. The body may have a first portion engaging the annular member and a second portion received into the bone, such that tightening the fastener against the annular member compresses the graft strands between opposing faces of the annular member and the head of the fastener.

Another embodiment of the invention provides a method for fastening a plurality of graft strands to a tunnel in a bone. The method may include pulling the graft strands through the tunnel and into a central opening of a first member, and inserting the graft strands into corresponding recesses radiating from the central opening. The method may include inserting a fastener through the first member and into the tunnel, and compressing the graft strands between the first member and the fastener.

Another embodiment of the invention provides another method for fastening a plurality of graft strands to a bone. The method may include drilling a bore for a fastener into the bone, drilling a counter bore for receiving first and second members into the bone and pulling the graft strands through a first opening in the first member and into corresponding radial recesses that extend from the first opening. The method may also include inserting the fastener through a second opening of the second member into the bore, engaging a threaded portion of the fastener with a portion of the first member, and compressing the graft strands between the first and second members.

BRIEF DESCRIPTION OF THE DRAWINGS

In the accompanying Figures, there are shown present embodiments of the invention, wherein like reference numerals are employed to designate like parts and wherein.

DETAILED DESCRIPTION OF THE INVENTION

Referring now to the drawings for the purpose of illustrating the invention and not for the purpose of limiting the same, it is to be understood that standard components or features that are within the purview of an artisan of ordinary skill and do not contribute to the understanding of the various embodiments of the invention are omitted from the drawings to enhance clarity. In addition, it will be appreciated that the characterizations of various components and orientations described herein as being "vertical" or "horizontal", "right" or "left", "upper", "lower", "distal", "proximal", "top" or "bottom", are relative characterizations only based upon the particular position or orientation of a given component for a particular application.

Figure 1:
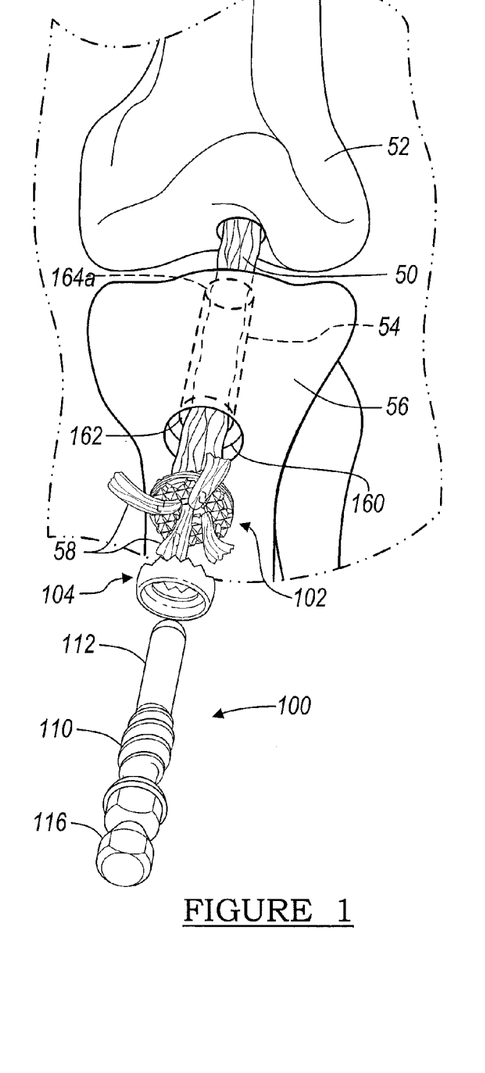
FIG. 1 is a diagram of a knee prepared for ACL reconstruction according to an embodiment of the fixation device of the present invention.

FIG. 1 is a simplified view of a knee prepared for ACL reconstruction and tibial fixation according to an embodiment of the present invention. A ligament or graft 50 extends from a femoral bone 52 and passes through a tunnel 54 that is bored into a tibial bone 56. The graft 50 may be bundled into several separate graft strands 58, such as four, for example. One example of a representative procedure to prepare the bore is set forth in U.S. Pat. No. 5,931,869, the entire contents of which are incorporated herein by reference. The graft 50 may be a natural graft harvested from the patient or from a donor using techniques that are known in the art. The graft 50 may also be synthetic, made from a polymer or other biocompatible material.

Figure 2:
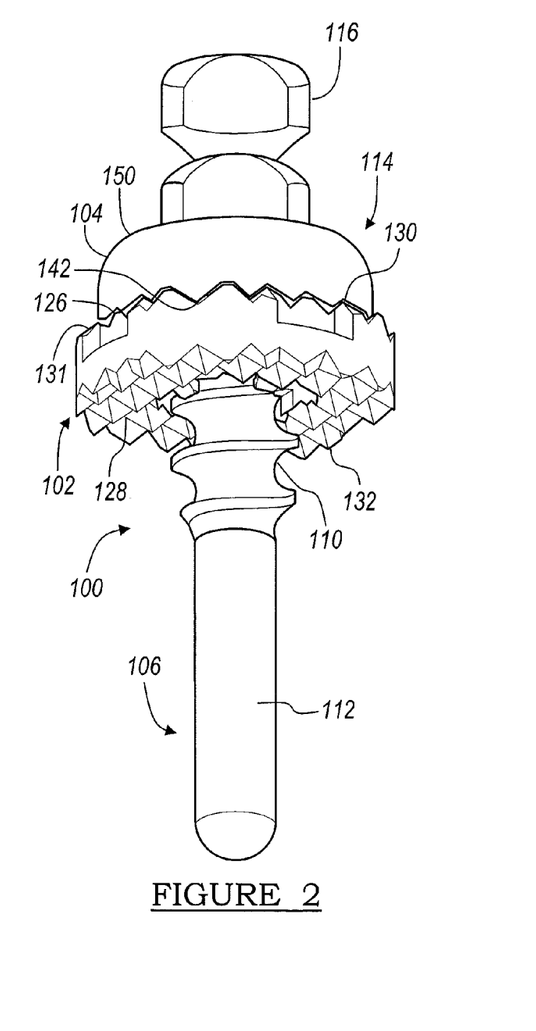
FIG. 2 is a perspective view of an embodiment of the fixation device of the present invention.
Figure 14:
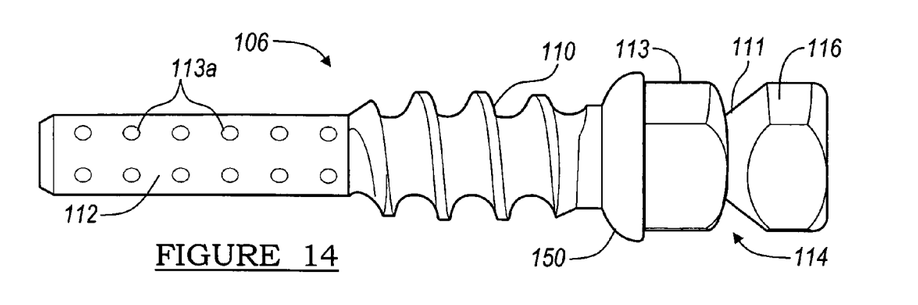
FIG. 14 is a side view of an embodiment of the fastener of the fixation device of the present invention.
Figure 15:
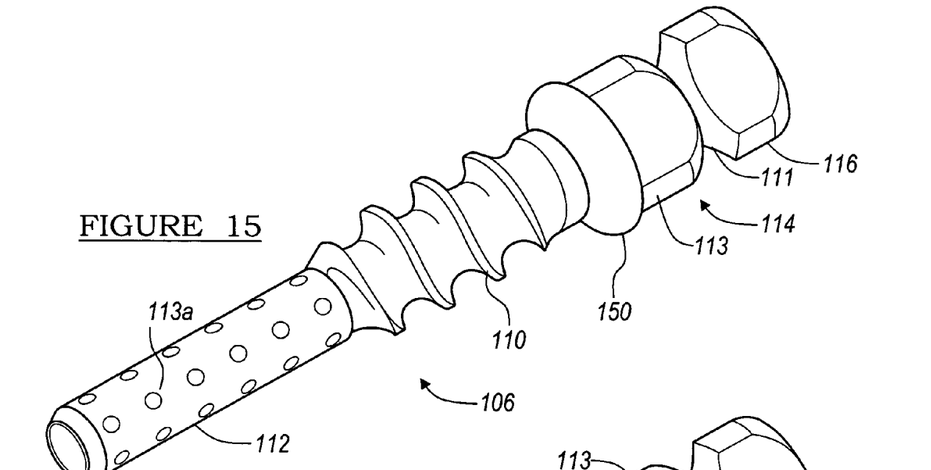
FIG. 15 is a perspective view of an embodiment of the fastener of the fixation device of the present invention.
Figure 16:
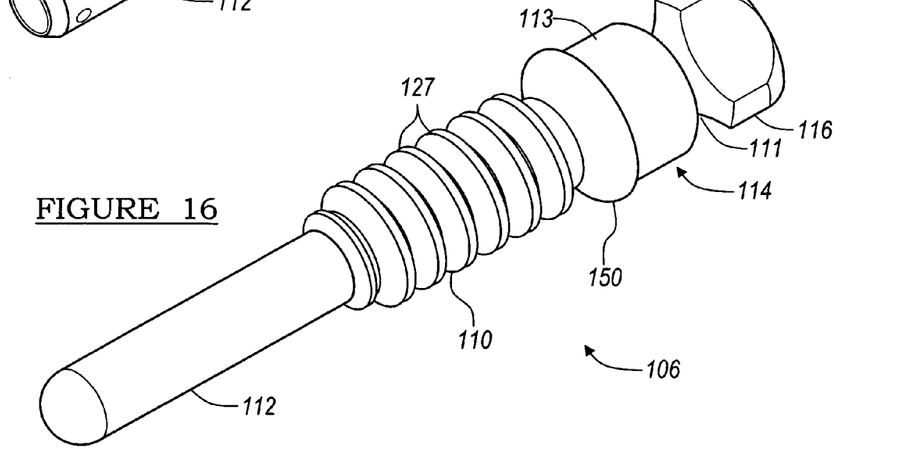
FIG. 16 is a perspective view of an embodiment of the fastener of the fixation device of the present invention.

FIG. 2 shows an embodiment of a fixation device or implant 100 that may be used to fasten the graft strands 58 into the tibial tunnel 54 during an ACL or similar procedure. The fixation device 100 may include a first member 102, a second member 104 and a fastener 106. The fastener 106 may include a body 108 having a first portion 110, which may be threaded or include concentric locking ribs 127, as shown in FIG. 16, and a second portion 112, which may also be threaded, or may be blank and act as a plug in the tunnel 54. In the embodiment shown in FIGS. 14 and 15, the second portion 112 of the fastener may be cannulated and may include a plurality of holes 113a to allow for graft passage.

Figure 3:
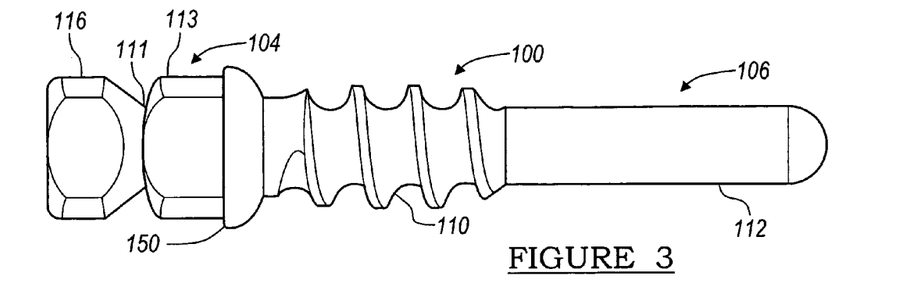
FIG. 3 is a side view of an embodiment of a fastener of the fixation device of the present invention.

The fastener 106 may also include a head 114, which may be tapered and/or segmented. In one aspect, the head 114 of the fastener 106 can include a top portion 116, a middle portion 113 and a lower portion 150. The top portion 116 can be tapered to a break away connection 111 to the middle portion 113, as shown in FIG. 3. The top portion 116 can be removed using a tool, such as a wrench or a socket, after attaching the fastener 106 to the tibial bone 56, to reduce the length of the fastener 106 after installation.

Figure 4:
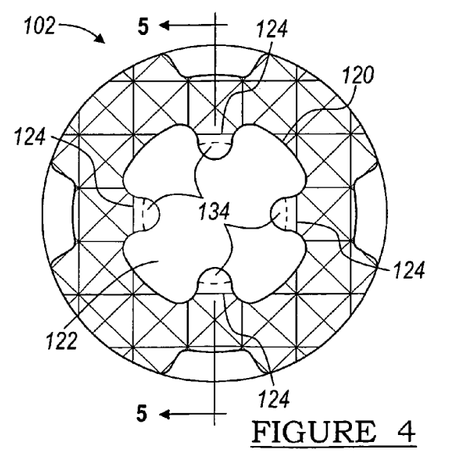
FIG. 4 is a top view of an embodiment of a first member of the fixation device of the present invention.

Referring to FIG. 4, the first member 102 includes a central opening 120 and a plurality of recesses or openings 122 that radiate from the central opening 120 and are separated by radial projections 124. In the embodiment shown in FIG. 4, the first member 102 includes four recesses 122 separated by four radial projections 124. The recesses 122 may be arranged to define a symmetric pattern, such as, for example, a cross, a four-petal cloverleaf, etc., although the recesses may also be arranged asymmetrically. The number of recesses 122 may be chosen to correspond to a maximum desirable number of graft strands 58. For example, the first member 102 may have four recesses 122, all of which may receive graft strands 58 in some applications, while in other applications only two recesses 122 may receive graft strands 58. The shape and the size of the recesses 122 may be determined to accommodate the size of the graft 50 and the size of the resulting graft strands 58.

Figure 5:
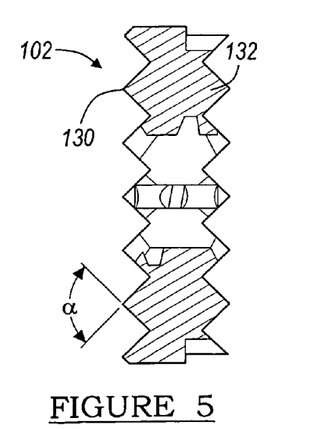
FIG. 5 is a sectional view of the first member taken along line 5-5 of FIG. 4.

In reference to FIGS. 2 and 5, the first member 102 has first and second faces 126,128. The first face 126 may include a plurality of protuberances 131, such as, for example, cleats or wedge-shaped protuberances, collectively wedges for short, 130. The second face 128 may also include a plurality of protuberances 131 or wedges 132. Each wedge 130, 132 may define an angle a, which may be selected such that the corresponding faces 126, 128 provide good grip without causing damage or tear to any bone or soft tissue surface that the wedge 130 may come into contact in use. The wedge angle a may be an obtuse angle, such as, for example, 96°. The wedges 130, 132 may be blunt and short rather than sharp and long. It will be appreciated that the protuberances 131 of the first member 102 may be other than wedge-shaped and may have, for example, circular or rectangular cross-sections.

As shown in FIG. 4, the radial projections 124 of the first member 102 may include segments 134, which may be threaded or otherwise shaped to engage the threaded portion 110 of the fastener 106 to enable the first member 102 to move up or down along the fastener 106 in a controllable and stable manner. In the embodiment shown in FIG. 11, the radial projections 124 include slots 125 that snap onto the locking ribs 127 of the first portion 110 of the fastener 106.

Figure 8A:
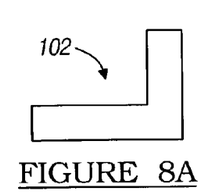
FIGS. 8(a)-(h) are diagrams of side profiles of various embodiments of the first member of the fixation device of the present invention.
Figure 8B:
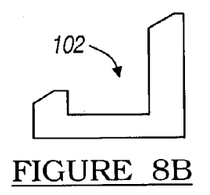
Figure 8C:
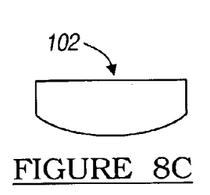
Figure 8D:
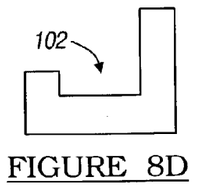
Figure 8E:
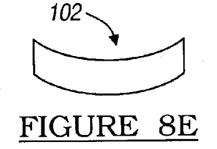
Figure 8F:
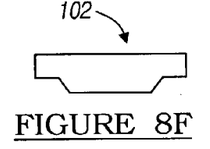
Figure 8G:
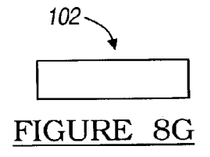
Figure 8H:
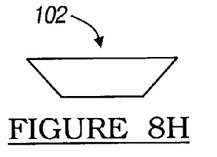

Referring to FIGS. 8(a)-8(h), the first member 102 may have a variety of side profiles, including: flat (rectangular), FIG. 8(g); tapered FIG. 8(h) and (f); curved, FIG. 8(e) and (c); L-shaped, FIG. 8(a); U-shaped, FIGS. 8(b) and (d); etc, or combinations thereof.

Figure 6:
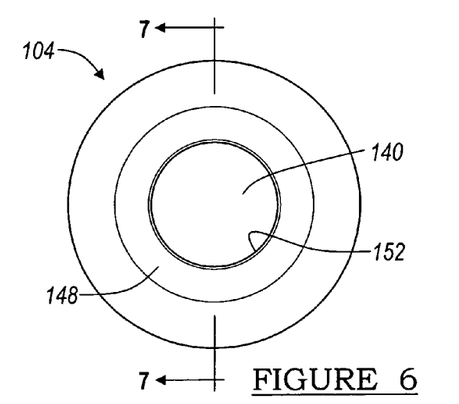
FIG. 6 a top view of an embodiment of a second member for the fixation device of the present invention.
Figure 7:
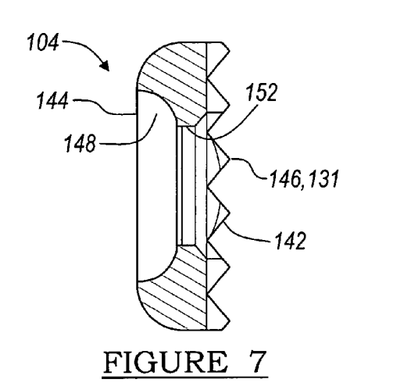
FIG. 7 is sectional view of the second member taken along line 7-7 of FIG. 6.

Referring to FIGS. 6 and 7, the second member 104 includes an opening 140 and has first and second faces 142, 144. The first face 142 of the second member 104 may include plurality of protuberances 131 or wedges 146 similar to those of the first member 102. The second face 144 of the second member may include a countersunk portion 148 sized to receive a lower portion 150 of the head 114 of the fastener 106. The inner surface 152 of the opening 140 may be undulated or threaded such that second member 104 can move along the threaded portion 110 of the fastener 106 in a controllable manner while in engagement with the fastener 106. The second member 104 may be pre-assembled onto the fastener 106 before the fastener 106 is inserted into the central opening 120 of the first member 102 and before the fixation device 100 is attached to the tibial bone 56.

In one embodiment, the second member 104 may be an integral portion of the fastener 106. In another embodiment, the second member 104 may be eliminated and its function may be assumed by the lower portion 150 of the head of the fastener.

The fixation device 100 may be implanted into the tibial bone 56 as follows. A step drill or other similar tool may be used to drill the tibial tunnel 54 to an appropriate length and size to receive the fixation device 100 as an implant. The step drill may create a counterbore 160 at a distal end 162 of the tunnel 54. The graft 50 may then be pulled in the tibial tunnel 54 through a proximal end 164a of the tibial tunnel 54 and out of the distal end 162. The graft 50 may be passed through the central opening 120 of the first member 102, which may be pulled up the graft 50 to be received into the counterbore 160 at the distal end 162 of the tibial tunnel 54. The graft strands 58 may be inserted into the individual recesses 122 of the first member 102 and made to lay flat and radially separated on the first face 126 of the first member 102. The fastener 106, having the second member 104 assembled thereon, may be threaded through the central opening 120 of the first member 102. When the fastener 106 is fully inserted into the tunnel 54, the graft strands 58 may be compressed against the tibial tunnel 54 and may also be securely compressed or clamped between the opposing surfaces 126 and 142 of the first and second members 102, 104.

In the embodiment in which the second member 104 is eliminated, the graft strands 58 may be compressed between the first member 102 and the lower portion 150 of the head 114 of the fastener. The top portion 116 of the head 114 of the fastener 106 may be twisted off with a wrench or similar tool, such that it does not protrude outside the tibial tunnel 54 and such that the fixation device 100 may implanted substantially in its entirety into the tibial tunnel 54 in a break-away manner.

In operation, the fastener 106 may be substantially coaxial with the tunnel 54. The first and second members 102, 104, which may be substantially planar, may be perpendicular to the tunnel 54 when inserted into the tunnel 54.

Figure 9:
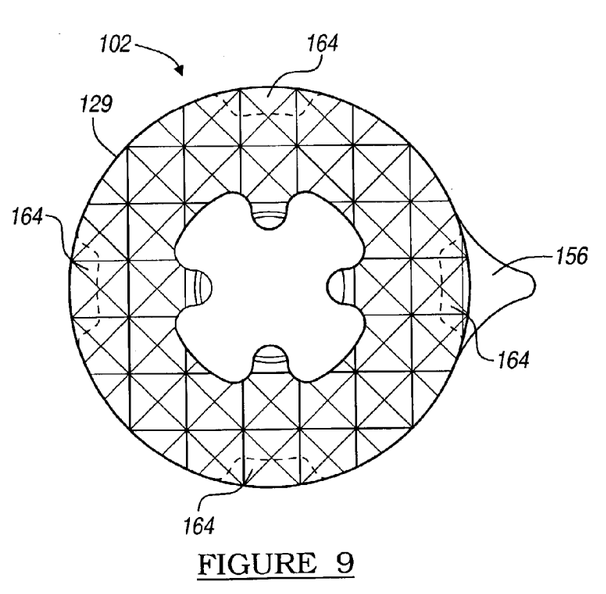
FIG. 9 is a top view of an embodiment of the first member of the fixation device of the present invention.
Figure 10:
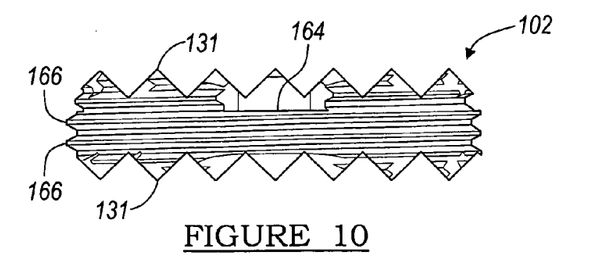
FIG. 10 is a perspective elevated view of an embodiment of the first member of the fixation device of the present invention.
Figure 11:
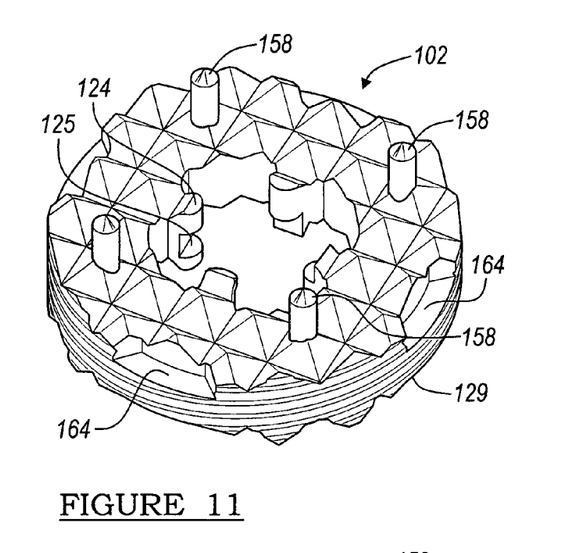
FIG. 11 is a perspective view of an embodiment of the first member of the fixation device of the present invention.
Figure 12:
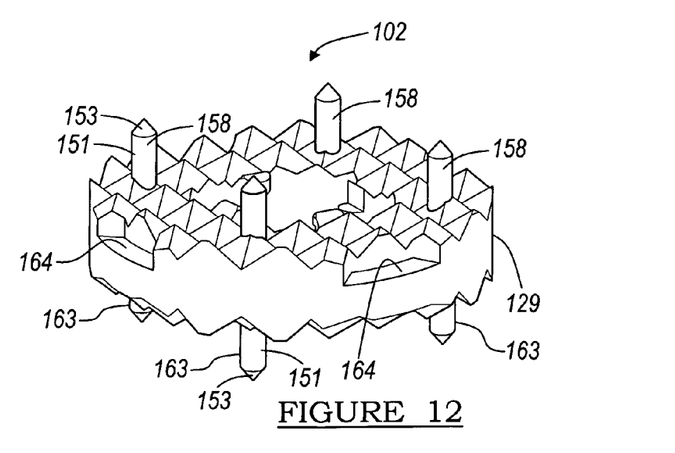
FIG. 12 is a perspective view of an embodiment of the first member of the fixation device of the present invention.
Figure 13:
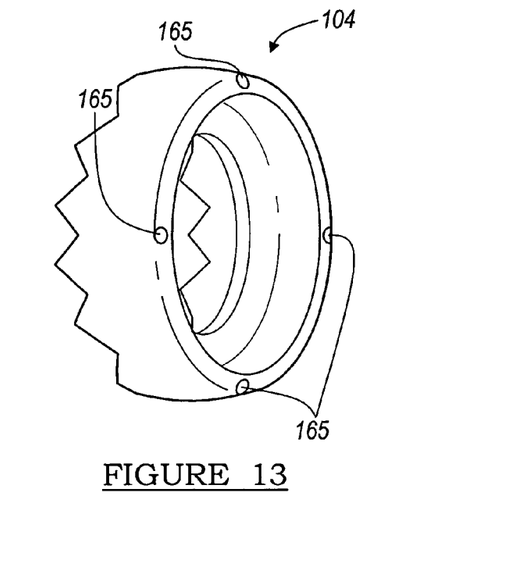
FIG. 13 is a perspective view of an embodiment of the second member of the fixation device of the present invention.

Referring to FIGS. 5, 9, 11 and 12, the first member 102 has a boundary surface 129, which may have a shape that is circular, or non-circular, such as, for example oval, rectangular, polygonal, etc. Referring to FIG. 10, the boundary surface 129 may include one or more outer peripheral formations 166, including ridges or grooves or threads, to provide better grip of the first member 102 in the tunnel 54. In the embodiment of FIG. 9, the first member includes an outer tab 156 to prevent the first member 102 from rotating after implantation. In the embodiment of FIG. 11, the first member 102 may include one or more top spikes 158 mating with corresponding apertures 160 of the second member 104. The first member 102 may also include one or more bottom spikes 163, as shown in FIG. 12. Each spike 158, 163 can include a cylindrical portion 151 and a pointed tip 153. Referring to FIGS. 9-12, the first member 102 may also include one or more substantially flat portions 164 for engagement with a tool holder that may be used to facilitate the installation of the first member.

Each of the components of the fixation device 100 may comprise one or more resorbable materials, such as LactoSorb®, or other polymeric materials, or bone graft material or other biocompatible materials, including metals, such as titanium or titanium alloy, stainless steel, etc. The use of resorbable material combined with implantation of the fixation device 100 in the tunnel 54 of the tibial bone 56 may promote circumferential healing in the tunnel 54. The first and second members 102, 104 may act as a cortical layer fixation device, in contrast with standard devices utilizing interference screws which only contact cancellous bone.

The counterbore 160 at the distal end 162 of the tunnel 54 may provide a ledge on which the first and second members 102, 104 may securely rest, thereby dispensing with the need to anchor the fixation device 100 with sharp long spikes into the bone, and avoiding an unnecessary risk of damage to the bone.

Whereas the fixation device 100 was described in connection with tibial bone fixation in an ACL procedure, it should be appreciated that the fixation device 100 may be readily used for securing grafts or ligaments in other types of bone and in other reconstruction procedures.

Furthermore, whereas particular embodiments of the invention have been described for the purpose of illustrating the invention and not for the purpose of limiting the same, it will be appreciated by those of ordinary skill in the art that numerous variations of the details, materials and arrangement of parts may be made within the principle and scope of the invention without departing from the spirit of the invention. The preceding description, therefore, is not meant to limit the scope of the invention. Rather the scope of the invention is to be determined only by the appended claims and their equivalents.

What is claimed is:

1. A device for fastening one or more graft strands to a bone, the device comprising:
a first member having a first central opening, the first central opening having a cross-section defined by a first pair of circumferential opposing recesses comprising two diametrically opposed recesses and a second pair of circumferential opposing recesses comprising two diametrically opposed recesses, the first pair of opposing recesses oriented at an angle to the second pair of opposing recesses, and first and second pairs of opposing radial projections, the circumferential recesses alternating sequentially with the radial projections, wherein each recess receives one of the graft strands;
a second member having a second central opening; and
a fastener passing through the first and second central openings, the fastener having a proximal portion engaging the first member and a distal portion received into the bone, such that tightening the fastener against the first member compresses the graft strands between opposing faces of the first and second members.

2. The device of claim 1, wherein the radial projections include threads and the proximal portion of the fastener is threaded and threadably engages the radial projections of the first member.

3. The device of claim 1, wherein the opposing faces of the first and second members include protuberances extending therefrom, the protuberances of the opposing faces adapted to intermesh and clamp and hold the graft strands therebetween.

4. The device of claim 3, wherein another face of the first member includes protuberances extending therefrom.

5. The device of claim 4, wherein the protuberances of the first and second members are wedge-shaped.

6. The device of claim 1, wherein the fastener and the first and second members comprise a resorbable material.

7. The device of claim 6, wherein the resorbable material is selected from the group consisting of metal, LactoSorb® and bone.

8. The device of claim 1, wherein the head of the fastener includes a narrow region between proximal and distal portions, the proximal portion having surfaces for engaging with a tool, the proximal portion being breakable at the narrow region off the distal portion.

9. The device of claim 8, wherein the second member includes a countersunk portion engaging the distal portion of the fastener's head.

10. The device of claim 1, wherein the proximal and distal portions of the fastener are received in a tunnel in the bone.

11. The device of claim 10, wherein the first and second members are countersunk in the tunnel.

12. The device of claim 10, wherein the fastener is sized for positioning co-axially in the tunnel.

13. The device of claim 10, wherein the first and second members are substantially perpendicular to the tunnel.

14. The device of claim 1, wherein the first and second members are substantially planar.

15. The device of claim 1, wherein the graft is an ACL replacement graft.

16. The device of claim 1, wherein the first member has a profile selected from the group consisting of flat, curved, tapered, L-shaped and U-shaped.

17. The device of claim 1, wherein the proximal portion of the fastener is threaded and the distal bone-engaging portion of the fastener is smooth.

18. The device of claim 1, wherein the second portion of the fastener is cannulated and includes holes therethrough.

19. The device of claim 1, wherein each radial projection includes a slot engaging a rib that extends radially from the first portion of the fastener.

20. The device of claim 1, wherein at least a portion of the fastener is cannulated.

21. The device of claim 1, wherein the second member has at least one aperture therethrough.

22. The device of claim 1 wherein the four recesses are arranged in opposing pairs defining a cross-like or four-petal cloverleaf shape.

23. The device of claim 1, wherein the first member includes a face having a plurality of protuberances interrupted by two diametrically opposed flat portions adapted to engage a tool holder.

24. The device of claim 1, wherein the first member includes at least one outer peripheral formation defined by one of a ridge, a groove, or a thread.

25. A device for fastening one or more graft strands to a bone, the device comprising:
  an annular member having a central opening, the central opening having a cross-section defined by a plurality of radial projections and a plurality of circumferential recesses, the circumferential recesses alternating sequentially with the radial projections, wherein each graft is operable to be separately received in one of the recesses, wherein a face of the annular member includes protuberances, the protuberances being interrupted by diametrically opposing flat portions adapted to engage a tool holder; and
  a fastener having a head and a body, the head having top, middle, and bottom portions, the top portion including outer tool-engagement surfaces and a narrowing break-away connection with the adjacent middle portion, the bottom portion adjacent to the middle portion and having an enlarged diameter relative to the middle portion, the body passing through the central opening of the annular member, the body having a proximal portion adjacent to the bottom portion of the head, the proximal portion being threaded and engaging the annular member, the body having a distal smooth portion adjacent the proximal portion, the distal portion received into the bone, such that tightening the fastener against the annular member compresses the graft strands between opposing faces of the annular member and the bottom portion of the head of the fastener.

26. The device of claim 25, wherein after the top portion of the head is broken off, the remaining portion of the fastener is entirely received into a tunnel in the bone.

27. The device of claim 25, wherein the bottom portion of the head of the fastener includes a protuberance facing the annular member.

28. The device of claim 25, wherein the annular member has an outer surface that has a circular shape.

29. The device of claim 25, wherein the central opening of the annular member is substantially cross-shaped.

30. A device for fastening one or more graft strands to a bone, the device comprising:
  an annular member having a central opening, the central opening having a cross-section defined by a plurality of radial projections and a plurality of circumferential recesses, the circumferential recesses alternating sequentially with the radial projections, wherein each graft is operable to be separately received in one of the recesses, wherein the annular member includes at least one outer peripheral formation defined by one of a ridge, a groove or a thread; and
  a fastener having a head and a body, the head having top, middle, and bottom portions, the top portion including outer tool-engagement surfaces and a narrowing break-away connection with the adjacent middle portion, the bottom portion adjacent to the middle portion and having an enlarged diameter relative to the middle portion, the body passing through the central opening of the annular member, the body having a proximal portion adjacent to the bottom portion of the head, the proximal portion being threaded and engaging the annular member, the body having a distal smooth portion adjacent the proximal portion, the distal portion received into the bone, such that tightening the fastener against the annular member compresses the graft strands between opposing faces of the annular member and the bottom portion of the head of the fastener.

31. A device for fastening one or more graft strands to a bone, the device comprising:
  an annular member having a central opening, the central opening having a cross-section defined by a plurality of radial projections and a plurality of circumferential recesses, the circumferential recesses alternating sequentially with the radial projections, wherein each graft is operable to be separately received in one of the recesses, wherein the annular member includes at least one spike integrally extended from a face of the annular member and including a smooth cylindrical portion adjacent to the face and an end portion having a pointed tip; and
  a fastener having a head and a body, the head having top, middle, and bottom portions, the top portion including outer tool-engagement surfaces and a narrowing break-away connection with the adjacent middle portion, the bottom portion adjacent to the middle portion and having an enlarged diameter relative to the middle portion, the body passing through the central opening of the annular member, the body having a proximal portion adjacent to the bottom portion of the head, the proximal portion being threaded and engaging the annular member, the body having a distal smooth portion adjacent the proximal portion, the distal portion received into the bone, such that tightening the fastener against the annular member compresses the graft strands between opposing faces of the annular member and the bottom portion of the head of the fastener.

32. An assembly for fastening one or more graft strands to a bone, the assembly comprising:
  a plurality of graft strands;
  a first member having a first central opening, the first central opening having a cross-section defined by a first pair of circumferential opposing recesses comprising two diametrically opposed recesses and a second pair of circumferential opposing recesses comprising two diametrically opposed recesses, the first pair of opposing recesses oriented at an angle to the second pair of opposing recesses, and first and second pairs of opposing radial projections, the circumferential recesses alternating sequentially with the radial projections, wherein each recess receives one of the plurality of graft strands;
  a second member having a second central opening; and
  a fastener passing through the first and second central openings, the fastener having a head and a body, the body having a first portion engaging the first member and a second portion received into the bone, such that tightening the fastener against the first member compresses the graft strands between opposing faces of the first and second members.

33. The assembly of claim 32, wherein the head includes top, middle, and bottom portions, the top portion including outer tool-engagement surfaces and a narrowing break-away connection with the adjacent middle portion, the bottom portion being adjacent to the middle portion and having an enlarged diameter relative to the middle portion, and wherein the first portion of the fastener is threaded and the second portion of the fastener is smooth.

34. An assembly for fastening one or more graft strands to a bone, the assembly comprising:
   at least two graft strands;
   a fastener defining a longitudinal axis, the fastener having a smooth distal portion, a threaded portion for engaging the bone, and a tool engaging portion;
   a first member defining a first opening for receiving the fastener, the first member defining at least a portion of four channels, each channel configured to selectively receive at least one graft strand, the first member having a first plurality of protuberances extending substantially parallel to the longitudinal axis of the fastener from a first face of the first member, the first member including a peripheral formation of threads; and
   a second member defining a second opening for receiving the fastener and having a second plurality of protuberances extending substantially parallel to the longitudinal axis of the fastener from a second face of the second member, the second face of the second member positioned such that the second plurality of protuberances is directed toward the first plurality of protuberances of the first face of the first member, wherein the at least two graft strands are captured between the first and second faces when the fastener is received through the first and second openings of the first and second members.

35. The assembly of claim 34 wherein the four channels are aligned along the longitudinal axis of the fastener.

* * * * *